United States Patent [19]

Kring

[11] Patent Number: 5,217,435
[45] Date of Patent: Jun. 8, 1993

[54] CARDIAC CATHETER APPARATUS

[76] Inventor: Robert S. Kring, 224 Markham Woods Rd., Longwood, Fla. 32779

[21] Appl. No.: 817,545

[22] Filed: Jan. 7, 1992

[51] Int. Cl.⁵ ............................................. A61M 5/28
[52] U.S. Cl. ................................. 604/164; 128/772
[58] Field of Search ............... 604/158, 164, 165, 170; 128/772

[56] References Cited

U.S. PATENT DOCUMENTS

| | | | |
|---|---|---|---|
| 4,230,123 | 10/1980 | Hawkins | 128/772 |
| 4,664,113 | 5/1987 | Frisbie et al. | 128/772 |
| 4,728,322 | 3/1988 | Walker et al. | 604/164 |
| 4,799,496 | 1/1989 | Hargreaves et al. | 128/772 |
| 4,844,092 | 7/1989 | Rydell et al. | 128/772 |
| 4,860,742 | 8/1989 | Park et al. | 128/772 |
| 5,011,473 | 4/1991 | Gatturna | 604/164 |

Primary Examiner—John J. Wilson
Assistant Examiner—L. Thomas
Attorney, Agent, or Firm—Pravel, Hewitt, Kimball & Krieger

[57] ABSTRACT

A device/apparatus that enhances the armamentarium of a physician in addressing coronary artery disease by providing the means by which a physician can have at his or her disposal two different and distinct PTCA balloon catheters in one. The device/apparatus is capable of converting a "movable wire balloon catheter" device into a "fixed wire balloon catheter" device, by merely attaching/connecting the (device/apparatus) wire converter system to the proximal center lumen of the wye connector housing of the "movable wire balloon catheter" device. The device/apparatus, wire converter system, could also be incorporated into the proximal wye connector housing of a "movable wire balloon catheter" device, thus enabling such a device to be convertible to a "fixed wire balloon catheter" device also. The device/apparatus, wire converter system, is also applicable as a standard wire torquing tool; to be used under routine application as are all other wire torque tools.

20 Claims, 2 Drawing Sheets

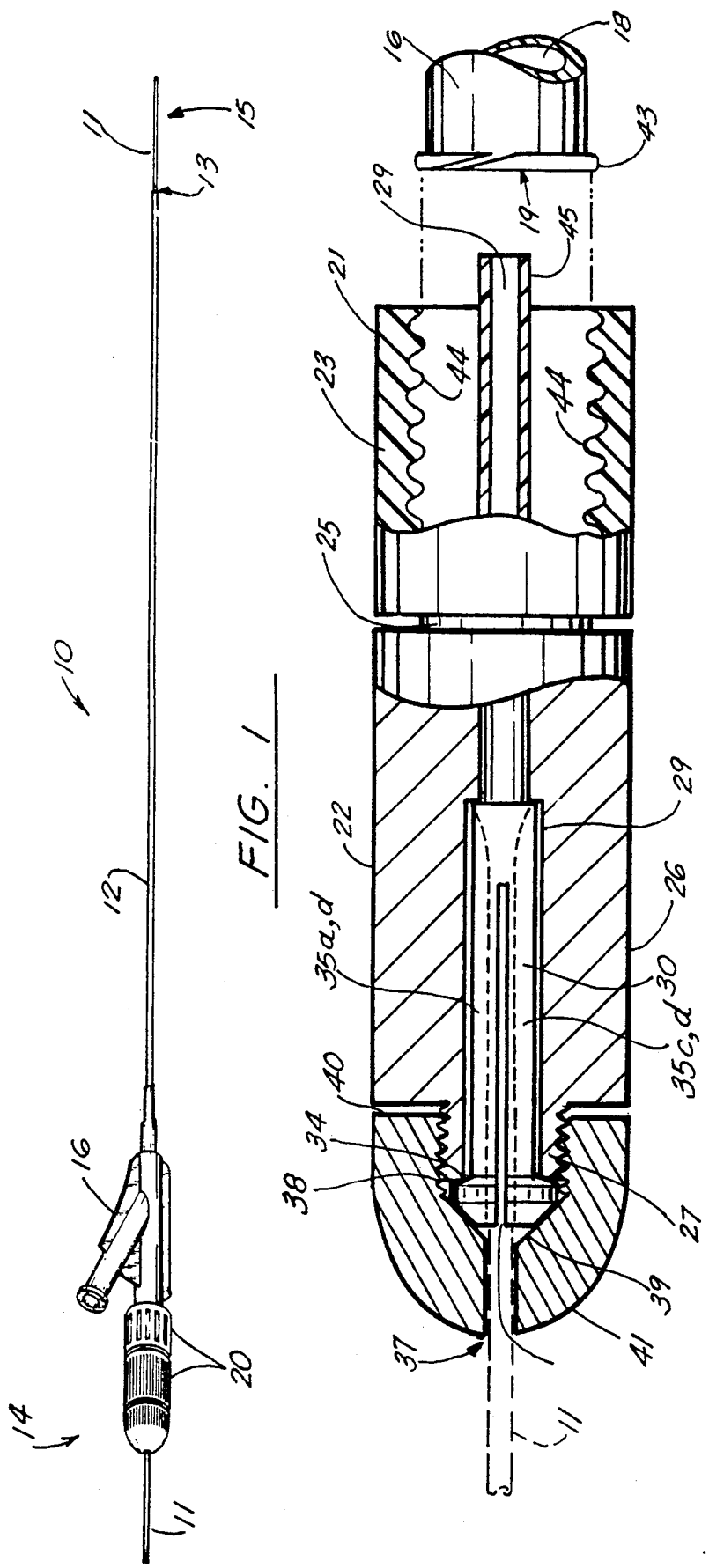

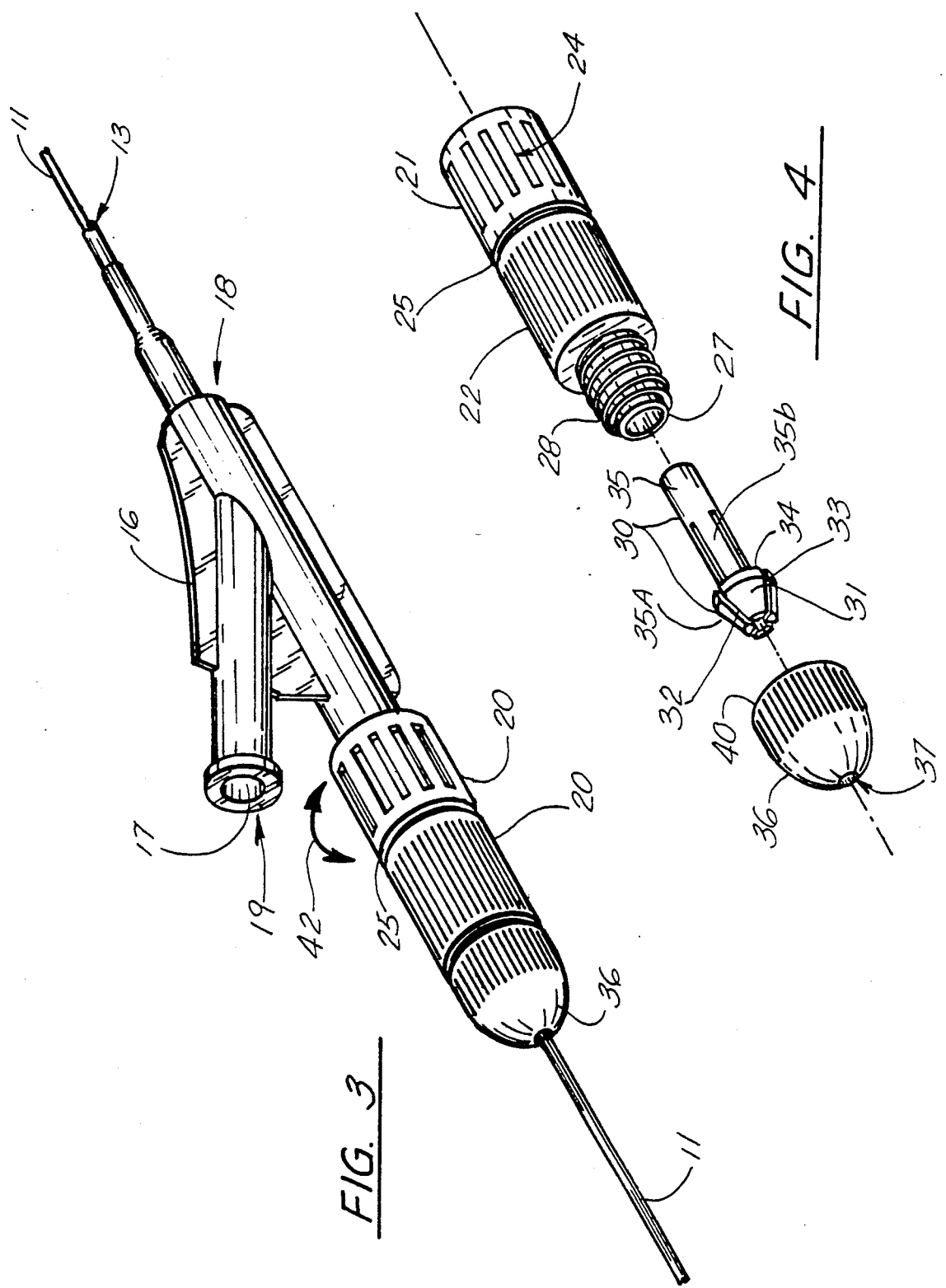

CARDIAC CATHETER APPARATUS

BACKGROUND OF THE INVENTION

1. Field of the Invention

The present invention relates to cardiac catheter devices and more particularly relates to an improved cardiac catheter apparatus that can be used in either percutaneous transluminal coronary angioplasty (PTCA) or percutaneous transluminal angioplasty (PTA) type catheter arrangements so that a convertible catheter apparatus is provided for optionally performing movable wire or fixed wire operations.

2. General Background

PTCA/PTA catheters were traditionally over the wire devices of either "fixed wire" configuration or "movable wire" configuration. These PTCA balloon catheter devices are used to recanalize and/or to re-perfuse blocked coronary arteries. Different anatomical layout, extent of coronary artery disease-blockage, and-/or type of lesion composition, all determine the type of device selected for use (i.e., fixed wire v. movable wire).

Today, physicians performing PTCA readily encounter and perform "complex angioplasty"; multi-lesion multi-vessel PTCA. Thus, multiple device usage (fixed wire and movable wire) during a single patient case is commonplace.

SUMMARY OF THE INVENTION

The PTCA wire converter system of the present invention is comprised of three separate functions combined in one single application providing the vehicle by which a physician can convert an over the wire PTCA device into a fixed wire PTCA device by merely attaching the PTCA wire converter system to the proximal end (center lumen) of the PTCA catheter. The PTCA catheter converter system is equally applicable to PTA balloon dilatation catheters devices employing a guide wire.

The apparatus consists primarily of a rotating connector such as a luhr lock connector, a wire crimping-/locking mechanism with hemostasis valve capabilities, and an overall housing/body portion. This apparatus converts any over the wire PTCA and/or PTA balloon dilatation device into a fixed wire PTCA and/or PTA balloon dilatation device. The operator (physician) can readily return to a movable over the wire mode should the circumstances warrant it.

The apparatus thus eliminates the need to change from an over-the-wire PTCA/PTA balloon dilatation device to a fixed wire device, should the operator (physician) require a different device in order to successfully accomplish a PTCA/PTA procedure.

The apparatus thus provides the capabilities for the operator (physician) to select virtually any desired fixed wire distal wire length: the length of the wire extending from the distal tip of the dilatation catheter (PTCA/PTA), i.e., 2.5 cm, 3 cm, 4 cm, 6 cm, etc.

The PTCA device of the present invention is applicable to all wires ranging between 0.010" and 0.018". The PTA wire converter system of the present invention device is applicable to all wires ranging between about 0.021" and 0.038".

The PTCA-PTA device of the present invention will directly result in the ability for a medical institution/-hospital performing interventional vascular dilatation to reduce its requirements for separate inventories of balloon devices with fixed wire systems. This advantage should reduce the operating burden of the hospital and reflect in lower costs.

The PTCA-PTA device of the present invention would provide added flexibility to the existing armamentarium of vascular dilatation balloons while reducing the need to exchange catheter systems, in the process of addressing the multitudinous complexities of arterial vessel obstructions, reduce the amount of procedure time, and increase the ability of the operator (physician) to successfully use the device of choice for the lesion (obstruction) being addressed.

The present invention provides an improved cardiac catheter apparatus which includes an elongated wire having a first end portion adapted to track a selected portion of the patient's vascular system. A catheter portion is provided which has a lumen sized to hold the wire. Both the wire and catheter portions are elongated, such as, for example, on the order of five-six (5-6) feet in length. A wye connector portion of the catheter defines the proximate end thereof and is used for manipulation of the catheter externally of the patient's vascular system. A body portion of the wire converter system of the present invention is attached to the wye connector. The wire converter system body includes first and second portions that are rotatably connected together, the first portion having a means for forming a removable attachment to the wye connector. The second end portion of the body includes means for selectively clamping the wire so that the wire can be rotated by rotation of the entire body.

The clamping means is selectively movable between clamped and released positions, and wherein the wire moves freely both longitudinally and rotatably with respect to the body in the released position, thereby defining a fixed wire or over the wire catheter apparatus as selected by the operator or physician.

The body preferably includes a longitudinally extending bore and the two body portions are attached by means of a swivel.

In the preferred embodiment, the connection of the body to the wye connector is a luhr type lock connection.

In the preferred embodiment, the body has a bore that slides over the wire during use.

The first body portion preferably has an open socket facing away from the second body portion, and wherein the wye connector affixes to the first body portion at the open socket.

The socket is preferably threaded to define the removable attachment between the body and the wye connector portion of the catheter.

The device of the present invention will thus enable the angioplasty physician to convert any "movably wire" balloon catheter into a "fixed wire" balloon catheter device should the need arise or be required. The device of the present invention is also readily applicable as a standard torquing tool as used with a movable wire balloon catheter system. The apparatus of the present invention will enable the angioplasty physician to have simultaneous access to two (2) different devices, while in fact using only one. The apparatus would double the flexibility and device armamentarium without noticeably increasing the cost of performing a PTCA. It could readily decrease and/or eliminate the use of an additional balloon catheters under many conditions or situations, a savings of many hundreds if not thousands of dollars to the hospital and patient.

The wire converter system of the present invention provides a stand along device for torquing the guide wire, when the wire locking mechanism is activated, but the apparatus is not attached to the proximal center lumen of the catheter wye connector. This enables the operator to freely advance, torque, and retract the attached guide wire independent of the PTCA catheter.

The operator/physician can lock the wire converter system to the proximal center lumen of the catheter wye connector and connect the movable wire PTCA catheter to a fixed wire PTCA catheter and adjust the length of wire extending beyond the distal tip of the balloon catheter in accordance to his or her preference and/or requirements. Thus two (2) distinct PTCA balloon devices are available at the cost of virtually one.

The apparatus of the present invention thus can comprise two separate devices. The stand along device can be used as an independent torquing tool and/or wire converter system that attaches to the movable wire balloon catheter converting it to a fixed wire balloon catheter. The wire converter system of the present invention can also be built into the proximal center lumen of wye connector housing of the removable wire balloon catheter.

Thus, the present invention provides either a stand along wire converter system or a built in wire converter system that enables the operator/physician to avail themselves of two different and distinct PTCA balloon catheter systems for addressing coronary artery disease/lesions/blockage.

Due to the complexities and changing circumstances encountered during complex angioplasty, the apparatus of the present invention could provide a measurable influence in reducing the amount of time required to complete a case by reducing the amount of catheter exchanges. The added advantage would be less x-ray exposure time, reduced patient risk factors, and general reduction in overall cardiac catheter lab costs. The same theory, principles, and applications, as described above are applicable to the Peripheral Angioplasty (PTA) devices and procedures such as iliac artery, SFA, renal artery, etc. The only change would be to enlarge the wire locking mechanism so that it would accommodate wires of larger diameters (i.e., 0.021, 0.025, 0.032, 0.035 inches) typically used in peripheral procedures.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a side view of the preferred embodiment of the apparatus of the present invention "luhr locked" to a PTCA balloon catheter;

FIG. 2 is a partial sectional view of the preferred embodiment of the apparatus of the present invention;

FIG. 3 is a perspective view of the preferred embodiment of the apparatus of the present invention; and FIG. 4 is an exploded perspective view of the preferred embodiment of the apparatus of the present invention.

DETAILED DESCRIPTION OF THE PREFERRED EMBODIMENT

FIGS. 1-4 illustrate generally the preferred embodiment of the apparatus of the present invention designated generally by the numeral 10. Catheter apparatus 10 includes an elongated wire 11 having end portions 11a, 11b. A tubular catheter 12 having an internal bore 13 accommodates the wire 11 along its length which can be, for example, approximately five-six (5-6) feet. The catheter 12 includes a proximate end 14 and a distal end 15 corresponding during operation to the end portions 11a, 11b respectively of wire 11. The wire external diameter can be between 0.010 and 0.18 inches and the bore 13 of catheter portion 12 provides an internal diameter substantially equal to or slightly larger than the external diameter of the wire 11.

A wye fitting 16 connects to the catheter 12, the wye fitting providing a lateral bore 17 and a straight line bore 18. Each of the bores 17, 18 provides openings 19.

A body portion 20 can be threadably attached to the wye fitting 16 using a luhr lock type connection, for example, (FIG. 2) wherein annular flange 43 attaches to internal threads 44 of body section 21. Tube 45 extends into bore 18 upon assembly. The body 20 includes a first body section 21 and a second body section 2. The first body section 21 provides a cylindrical outer wall 23 having a gripping surface 24 thereon. The first body portion 21 is rotatably attached to the second body portion 22 with swivel 25. The second body portion 22 provides a cylindrical outer wall 26. One end portion of the second body 22 has an externally threaded section 27 with threads 28. A longitudinally extending bore 29 extends the length of the body 20.

Wedge member 30 connects to the body 20 at the cylindrical section 35 thereof. The wedge member 30 includes a conical section 31 which is cut by a pair of longitudinally extending flat slots 32, 34 which intersect at right angles with respect to each other. An annular shoulder 34 is also provided on the wedge member 30. End cap 36 provides a bore 37 accommodating wire 11 and a thicker portion 37a of bore 37 has internal threads 38. The inside surface of end cap 36 provides a conical surface 39 that engages the conical surface 31 of the wedge member 30. Cap 36 can have a hemispherical outer surface 41. Wedge member 30 rests against annular shoulder 41 when cap 36 is tightened. Arrow 42 indicates a rotational movement of the body 20. When threads 38 of the end cap 36 are tightened upon the threads 28 of externally threaded section 27, this forces the conical surface 39 of end cap 36 to compress against the wedge member 30 and to compress the longitudinal slots 32, 33 narrowing the thickness of these slots, so that the cylindrical section 35 of wedge member 30 grips wire 11. The cylindrical section 35 is formed of four (4) quarter sections 35a-d which bend to grip wire 11.

| PARTS LIST | |
|---|---|
| Part Number | Description |
| 10 | catheter apparatus |
| 11 | wire |
| 12 | catheter |
| 13 | bore |
| 14 | proximate end |
| 15 | distal end |
| 16 | wye fitting |
| 17 | lateral bore |
| 18 | straight bore |
| 19 | opening |
| 20 | body |
| 21 | first body section |
| 22 | second body section |
| 23 | cylindrical outer wall |

-continued

PARTS LIST

| Part Number | Description |
| --- | --- |
| 24 | gripping surface |
| 25 | swivel |
| 26 | cylindrical outer wall |
| 27 | externally threaded section |
| 28 | threads |
| 29 | longitudinal bore |
| 30 | wedge member |
| 31 | conical section |
| 32 | longitudinal slot |
| 33 | longitudinal slot |
| 34 | annular shoulder |
| 35 | cylindrical section |
| 35 a–d | quarter sections |
| 36 | end cap |
| 37 | bore |
| 38 | internal threads |
| 39 | conical surface |
| 40 | annular shoulder |
| 41 | hemispherical surface |
| 42 | arrow |
| 43 | flange |
| 44 | internal thread |
| 45 | annular tube |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A cardiac catheter apparatus, comprising:
   a) an elongated wire having a first end portion adapted to track a selected portion of a patient's vascular system;
   b) a catheter portion having a lumen sized to hold the wire;
   c) a wye connector portion of the catheter defining the proximate end thereof, the wye connector having a first straight bore portion and a laterally extending bore that intersects the straight bore for manipulation of the catheter and wire externally of the patient's vascular system;
   d) a body portion that is threadably and removably attachable to the wye connector for movement therewith, the body having first and second end portions that are rotatably connected together, the first portion having means for forming a removable attachment to said wye connector;
   e) the second end portion of the body having means for selectively clamping the wire so that the wire can be rotated by rotation of the body;
   f) said clamping means being able to grip the wire so that the wye connector and body in combination can rotate with the wire; and
   g) an attachment of the body to the wye connector enabling a conversion from a movable over the wire to a fixed wire balloon catheter system.

2. The apparatus of claim 1 wherein the body includes a longitudinally extending bore.

3. The apparatus of claim 1 wherein the connecting means is a luhr lock connection.

4. The apparatus of claim 1 wherein the body has a bore that slides over the wire and catheter during use.

5. The apparatus of claim 1 wherein there is provided a hemostasis valve.

6. The apparatus of claim 1 wherein the first body portion has an open socket facing away frog the second body portion.

7. The apparatus of claim 6 wherein the socket is threaded to define the removable attachment means.

8. The apparatus of claim 7 wherein the first body portion has a longitudinally extending bore that traverses the socket, and the body includes a peripheral wall surrounding the socket, and there are internal threads on the internal wall forming the removable attachment means.

9. The apparatus of claim 1 further comprising a swivel, and wherein the first and second body portions are attached together at the swivel.

10. A percutaneous vascular balloon catheter apparatus comprising:
    a) a catheter having a bore, and proximal and distal end portions;
    b) the catheter having a wire insertable into a patient's vascular system and being of a length that allows a cardiologist to manipulate the wire into selected portions of the patient's vascular system;
    c) a housing having first and second end portions;
    d) a rotating wye-connector portion that attaches to the housing the wye-connector portion including first and second bores that angularly intersect, the first bore forming an acute angle with the second bore;
    e) wherein the second bore extends longitudinally through the housing and rotating connector, the wire and catheter portions being insertable through the second bore so that the wire is movable with respect to the housing at the second bore; and
    f) locking means on the housing for securing the housing and connector together and the wire portion with respect to the housing, so that the housing can be gripped and torqued for transferring torque to the wire portion.

11. The apparatus of claim 10 wherein the housing is generally cylindrical.

12. The apparatus of claim 10 wherein the housing is of a generally uniform cross section.

13. The apparatus of claim 10 wherein the wire portion is of a diameter of between 0.010–0.028 inches.

14. The apparatus of claim 10 further comprising a socket portion of the housing, and wherein the socket is positioned on the body opposite the locking means.

15. The apparatus of claim 10 wherein the locking means threadably attaches to the body.

16. The apparatus of claim 10 wherein the housing is a two part housing that includes first and second housing sections that are rotatably connected together.

17. The apparatus of claim 10 wherein the socket is positioned at a first end portion of the body that is connectable during use to the proximal end of a PTCA-PTA catheter.

18. The apparatus of claim 10 wherein the wire member is of an external diameter of about 0.010–0.035 inches.

19. The apparatus of claim 10 further comprising a swivel and wherein the housing is comprised of first and second body portions connected together at the swivel.

20. The apparatus of claim 14 wherein the socket is internally threaded.

* * * * *